(12) United States Patent
Gaur

(10) Patent No.: US 10,065,020 B2
(45) Date of Patent: Sep. 4, 2018

(54) DELIVERY APPARATUS

(71) Applicant: University Hospitals of Leicester NHS Trust, Leicestershire (GB)

(72) Inventor: Atul Gaur, Leicestershire (GB)

(73) Assignee: University Hospitals of Leicester NHS Trust, Leicestershire (GB)

( * ) Notice: Subject to any disclaimer, the term of this patent is extended or adjusted under 35 U.S.C. 154(b) by 0 days.

(21) Appl. No.: 14/410,407

(22) PCT Filed: Jul. 3, 2013

(86) PCT No.: PCT/GB2013/051763
§ 371 (c)(1),
(2) Date: Dec. 22, 2014

(87) PCT Pub. No.: WO2014/006403
PCT Pub. Date: Jan. 9, 2014

(65) Prior Publication Data
US 2015/0328434 A1    Nov. 19, 2015

(30) Foreign Application Priority Data

Jul. 3, 2012  (GB) .................................. 1211745.3

(51) Int. Cl.
*A61M 25/00* (2006.01)
*A61M 25/01* (2006.01)
(Continued)

(52) U.S. Cl.
CPC ....... *A61M 25/0097* (2013.01); *A61B 8/0841* (2013.01); *A61B 8/12* (2013.01); *A61M 5/427* (2013.01); *A61M 25/0026* (2013.01); *A61M 25/0108* (2013.01); *A61M 25/0643* (2013.01); *A61B 17/3496* (2013.01); *A61B 2017/3413* (2013.01); *A61B 2017/3445* (2013.01); *A61M 2005/3212* (2013.01); *A61M 2025/0001* (2013.01); *A61M 2025/004* (2013.01);
(Continued)

(58) Field of Classification Search
None
See application file for complete search history.

(56) References Cited

U.S. PATENT DOCUMENTS 3,827,434 A * 8/1974 Thompson .......... A61M 25/065
604/160
3,941,121 A * 3/1976 Olinger ............. A61B 1/00188
385/117
(Continued)

FOREIGN PATENT DOCUMENTS

EP    0125843    5/1984
EP    1106201    6/2001
(Continued)

*Primary Examiner* — Tse Chen
*Assistant Examiner* — Joanne Hoffman
(74) *Attorney, Agent, or Firm* — Pabst Patent Group LLP

(57) ABSTRACT

A delivery apparatus is provided for inserting catheters and/or cannulae into a patient's blood vessel or body cavity either with or without the use of ultrasound imaging. The apparatus is used for the delivery of central venous catheters (CVCs) for creating a central line. The invention also relates to uses of the apparatus, and to methods for inserting catheters or cannulae (e.g. a CVC) into a patient.

19 Claims, 10 Drawing Sheets

(51) Int. Cl.
  *A61B 8/12* (2006.01)
  *A61M 5/42* (2006.01)
  *A61B 8/08* (2006.01)
  *A61M 25/06* (2006.01)
  *A61M 5/32* (2006.01)
  *A61B 17/34* (2006.01)

(52) U.S. Cl.
  CPC ............ *A61M 2025/0031* (2013.01); *A61M 2025/0036* (2013.01); *A61M 2205/3344* (2013.01); *A61M 2210/12* (2013.01)

(56) References Cited

U.S. PATENT DOCUMENTS

| | | | | |
|---|---|---|---|---|
| 4,160,450 | A * | 7/1979 | Doherty | A61M 25/0606 604/162 |
| 4,417,886 | A * | 11/1983 | Frankhouser | A61M 25/0606 600/435 |
| 4,600,014 | A * | 7/1986 | Beraha | A61B 10/0241 600/567 |
| 4,966,162 | A * | 10/1990 | Wang | A61B 10/04 600/563 |
| 5,004,456 | A * | 4/1991 | Botterbusch | A61M 25/0054 604/158 |
| 5,111,828 | A * | 5/1992 | Kornberg | A61B 10/0266 600/567 |
| 5,197,484 | A * | 3/1993 | Kornberg | A61B 10/0266 600/567 |
| 5,255,691 | A * | 10/1993 | Otten | A61N 1/0551 607/117 |
| 5,300,045 | A * | 4/1994 | Plassche, Jr. | A61M 5/3273 604/158 |
| 5,312,345 | A * | 5/1994 | Cole | A61M 25/0643 604/110 |
| 5,312,361 | A * | 5/1994 | Zadini | A61M 5/158 604/165.02 |
| 5,474,543 | A * | 12/1995 | McKay | A61B 17/0469 604/272 |
| 5,496,281 | A * | 3/1996 | Krebs | A61B 17/3401 604/168.01 |
| 5,527,290 | A * | 6/1996 | Zadini | A61M 5/158 604/157 |
| 5,569,291 | A * | 10/1996 | Privitera | A61B 17/3417 606/185 |
| 5,578,053 | A | 11/1996 | Yoon | |
| 5,579,774 | A * | 12/1996 | Miller | A61B 5/031 600/479 |
| 5,582,190 | A * | 12/1996 | Slavin | A61B 1/015 128/898 |
| 5,681,276 | A * | 10/1997 | Lundquist | A61B 18/1477 604/22 |
| 5,738,628 | A * | 4/1998 | Sierocuk | A61B 17/3421 600/104 |
| 5,795,339 | A * | 8/1998 | Erskine | A61M 25/0631 604/171 |
| 5,810,841 | A * | 9/1998 | McNeirney | A61B 17/3403 33/286 |
| 5,941,850 | A * | 8/1999 | Shah | A61M 5/3232 604/110 |
| 6,030,402 | A * | 2/2000 | Thompson | A61B 17/3494 606/105 |
| 6,102,887 | A * | 8/2000 | Altman | A61M 25/0084 604/22 |
| 6,283,958 | B1 * | 9/2001 | Vogl | A61M 25/0662 606/10 |
| 6,770,070 | B1 * | 8/2004 | Balbierz | A61B 10/04 600/566 |
| 7,935,108 | B2 * | 5/2011 | Baxter | A61B 18/1492 606/15 |
| 2001/0018572 | A1 | 8/2001 | Kinsey | |
| 2002/0007104 | A1 * | 1/2002 | Kaplan | A61M 37/0069 600/7 |
| 2002/0095123 | A1 | 7/2002 | Smutney | |
| 2002/0169377 | A1 * | 11/2002 | Khairkhahan | A61B 5/0084 600/433 |
| 2003/0120222 | A1 * | 6/2003 | Vaillancourt | A61M 5/321 604/263 |
| 2004/0116864 | A1 * | 6/2004 | Boudreaux | A61M 25/0643 604/164.01 |
| 2004/0133168 | A1 * | 7/2004 | Salcudean | A61B 10/04 604/164.13 |
| 2004/0138527 | A1 * | 7/2004 | Bonner | A61B 18/1485 600/114 |
| 2005/0054900 | A1 * | 3/2005 | Mawn | A61B 1/3132 600/156 |
| 2005/0090763 | A1 * | 4/2005 | Wang | A61B 10/04 600/564 |
| 2005/0288622 | A1 * | 12/2005 | Albrecht | A61B 17/3417 604/23 |
| 2007/0021767 | A1 * | 1/2007 | Breznock | A61B 17/00234 606/185 |
| 2007/0060889 | A1 * | 3/2007 | Adams | A61B 17/3415 604/164.01 |
| 2008/0097487 | A1 * | 4/2008 | Pool | A61F 5/003 606/151 |
| 2009/0018507 | A1 * | 1/2009 | Schmitz | A61B 17/1757 604/164.03 |
| 2009/0177090 | A1 * | 7/2009 | Grunwald | A61B 5/026 600/454 |
| 2009/0192444 | A1 * | 7/2009 | Albrecht | A61B 17/3474 604/26 |
| 2010/0048990 | A1 * | 2/2010 | Bakos | A61B 17/3478 600/106 |
| 2010/0081988 | A1 * | 4/2010 | Kahle | A61B 17/3417 604/26 |
| 2010/0210934 | A1 * | 8/2010 | Belson | A61M 25/0105 600/371 |
| 2011/0282188 | A1 * | 11/2011 | Burnside | A61B 5/042 600/424 |
| 2011/0301580 | A1 * | 12/2011 | Hoffman | A61F 2/20 606/1 |
| 2012/0071857 | A1 * | 3/2012 | Goldfarb | A61B 17/24 604/514 |
| 2012/0265051 | A1 * | 10/2012 | Fischer | A61B 10/0241 600/411 |
| 2013/0267980 | A1 * | 10/2013 | Torrie | A61B 17/3496 606/185 |
| 2013/0310750 | A1 * | 11/2013 | Hopman | A61M 1/008 604/159 |
| 2013/0345512 | A1 * | 12/2013 | Smith | A61B 1/00154 600/114 |
| 2014/0249371 | A1 * | 9/2014 | Fischvogt | A61B 17/3417 600/114 |

FOREIGN PATENT DOCUMENTS

| | | |
|---|---|---|
| EP | 1110575 | 6/2001 |
| EP | 1110576 | 6/2001 |
| WO | 2002062410 | 8/2002 |

* cited by examiner

A)

B)

C)

D)

E)

F)

G)

DELIVERY APPARATUS

FIELD OF THE INVENTION

The invention relates to delivery apparatus for inserting catheters and/or cannulae into a patient's blood vessel or body cavity either with or without the use of ultrasound imaging. In particular, the invention concerns the delivery of central venous catheters (CVCs) for creating a central line. The invention also relates to uses of the apparatus, and to methods for inserting catheters or cannulae (e.g. a CVC) into a patient.

BACKGROUND OF THE INVENTION

CVCs are used primarily to gain access to the venous system of a patient for administering intravenous therapy, such as drugs, chemotherapy, and total parenteral nutrition. They can also be used to provide access to the patient for blood sampling and central venous pressure monitoring. The most common technique used by a clinician to gain access to the central venous system of the patient with a CVC is a landmark guided technique known as the Seldinger technique, which is illustrated in FIG. 1. This technique involves the clinician first inserting a needle 2 through the patient's skin 4 at a peripheral location and into a vein to form a venotomy (FIG. 1a). A blunt guidewire 6 is then passed through the channel of the needle 2 (FIG. 1b), and then the needle 2 is removed (FIG. 1c). Next, a dilating device 8 is passed over the guidewire 6 to slightly enlarge the tract originally produced by the needle 2 (FIG. 1d), and then make way for a catheter 10, which is then passed over the guidewire 6 (FIG. 1e). Finally, the guidewire 6 is removed from the patient leaving the catheter 10 in position (FIG. 1f). All channels in the catheter are then aspirated and flushed with saline to ensure that they are all positioned inside the vein.

However, many problems have presented themselves in terms of how effectively a CVC can be deployed in and along a patient's vein using the above multi-step technique, especially with the use of real-time ultrasound imaging, and how this might impact, not only on the comfort of the patient, but also any medical risks that could be presented to the patient as a result. For example, such landmark guided techniques may be more commonly associated with accidental injury to adjacent structures such as the carotid artery, with serious consequences such as stroke or aneurysm formation, thereby increasing morbidity in patients. Hence, the National Institute of Clinical Excellence has provided some assistance concerning the use of ultrasound in these techniques in order to minimize such mishaps. However, a purpose-built central venous catheter for use under ultrasound guidance does not currently exist, and so catheters usually intended to be used in landmark guided techniques, e.g. Seldinger technique, are still being used. Other problems associated with deployment include how to keep the catheter or a surrounding region sufficiently sterile using the Seldinger technique referred to above, especially with the use of ultrasound.

SUMMARY OF THE INVENTION

In order to achieve maximum safety, as well as comfort and minimum risk to a patient there is therefore a need for a catheter or cannula delivery device, which can be easily and more comfortably deployed by the clinician, for example while using ultrasound guidance.

BRIEF DESCRIPTION OF THE DRAWINGS

For a better understanding of the invention, and to show how embodiments of the same may be carried into effect, reference will now be made, by way of example, to the accompanying diagrammatic drawings, in which:—

DETAILED DESCRIPTION OF THE INVENTION

Figure 1:
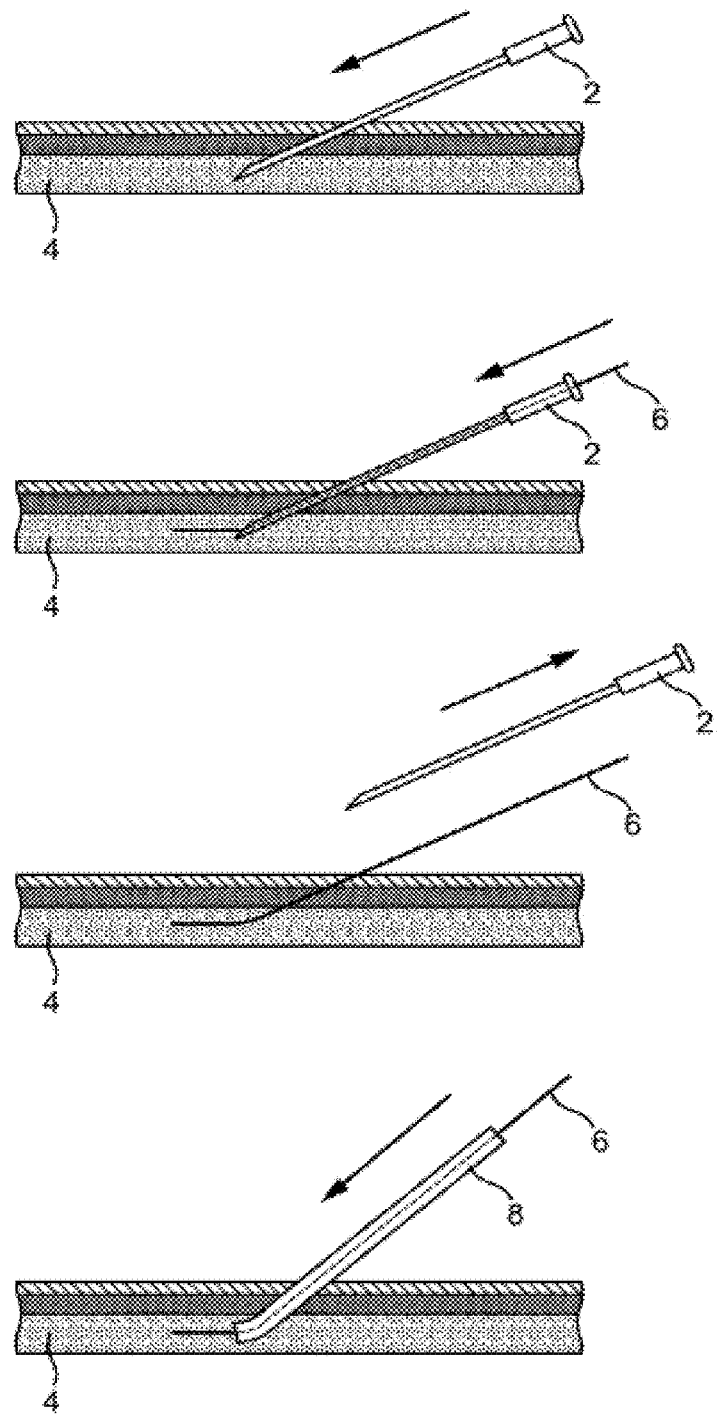
FIG. 1 illustrates a prior art, multi-step Seldinger technique for gaining access to the central venous system of a patient with a central venous catheter (CVC)
Figure 1:
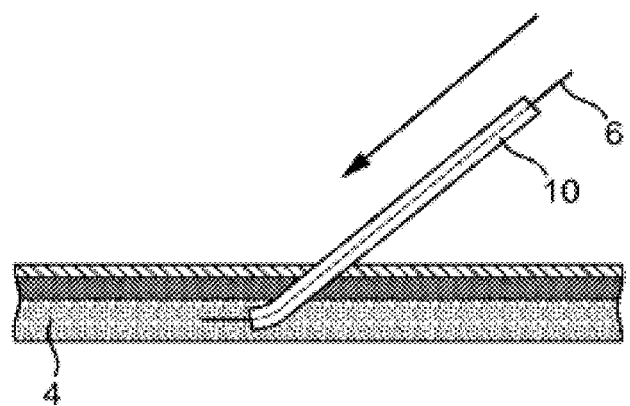
Figure 1:
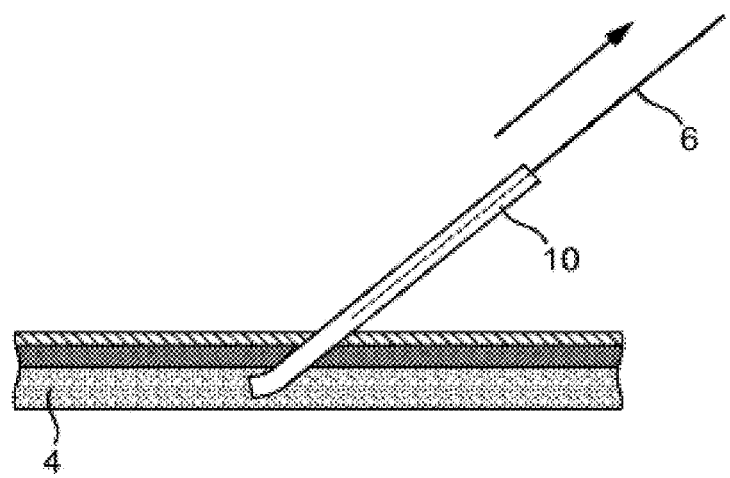
Figure 2:
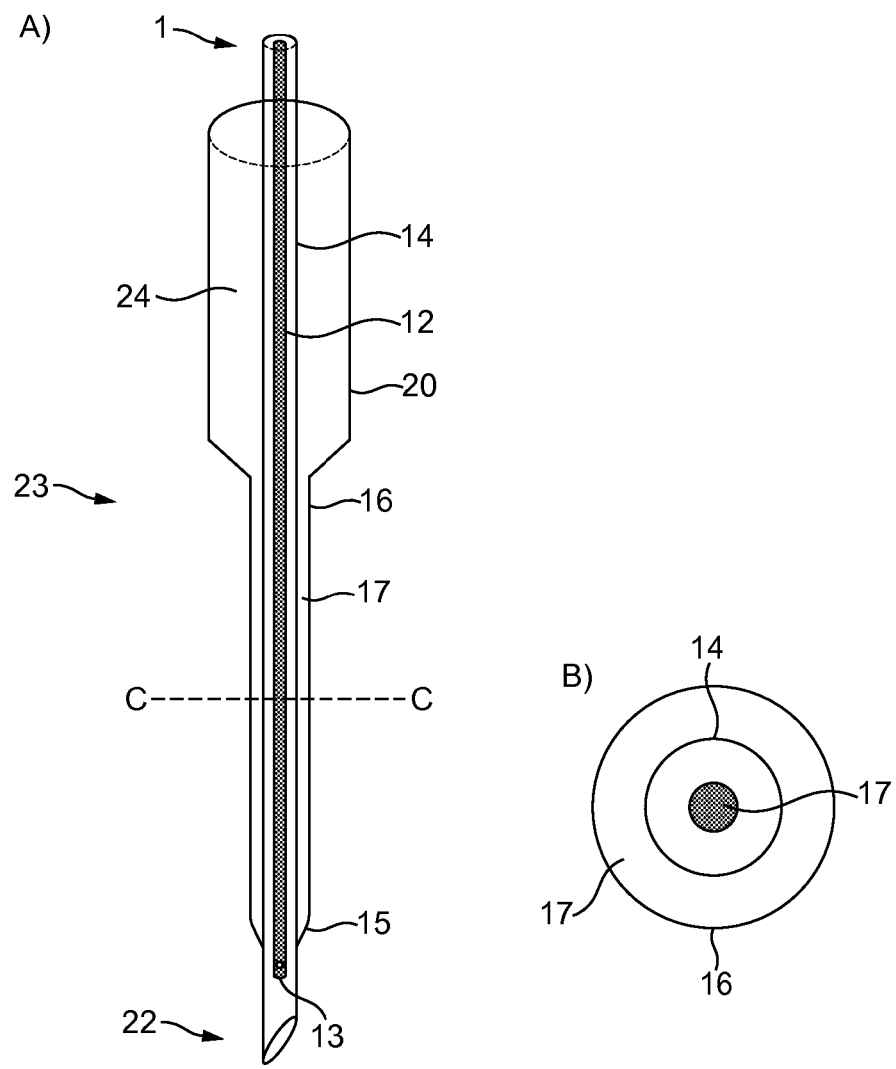
FIG. 2A is a schematic cross-sectional side view of a cannula component of an apparatus of the invention, for use in inserting a CVC into a patient.
FIG. 2B is a cross-sectional plan view of the cannula along axis C-C of FIG. 2A.

According to a first aspect of the invention, there is provided a delivery apparatus for introducing a catheter or cannula into a subject's vessel or body cavity, the apparatus comprising:—

(i) a catheter or cannula comprising at least one channel extending therethrough and through which access to a subject's vessel or body cavity is achieved, (ii) a removable needle extending through the catheter or cannula, the needle comprising a stellate slideably disposed therein; and (iii) an adapter comprising at least one channel extending therethrough, and arranged, in use, to be attached to the catheter or cannula following removal of the needle and stellate from the subject, such that the at least one channel in the adaptor aligns with the at least one channel in the catheter or cannula to thereby create at least one continuous passageway through which access to the subject's vessel or body cavity is achieved.

In a second aspect, the invention provides the delivery apparatus of the first aspect, for use in diagnosis or therapy.

In a third aspect, the invention provides the delivery apparatus of the first aspect, for use in obtaining a sample from a subject; draining fluid from a subject; administering medication or fluid to a subject; for monitoring a subject; or for carrying out a cardiovascular measurement on a subject.

In a fourth aspect, there is provided a method for introducing a catheter or cannula into a subject, the method comprising attaching the delivery apparatus of the first aspect to a subject, and introducing the catheter or cannula into a vessel or body cavity of the subject.

In a fifth aspect, there is provided a method for obtaining a sample from a subject, or draining fluid from a subject, or administering medication or fluid to a subject, or monitoring a subject, or for carrying out a cardiovascular measurement on a subject, the method comprising use of the delivery apparatus according to the first aspect.

Advantageously, the delivery apparatus of the invention can be simply and safely introduced into a subject's (e.g. a patient) vessel (e.g. an artery or vein) or body cavity, in a single-step procedure without the need to use a dilator or guidewire, and without any interruptions when using ultrasound imaging or guidance. Since the use of the apparatus of the invention involves a single-step procedure, it takes much less time, and is therefore much quicker to carry out. The delivery method of the fourth aspect is therefore significantly easier to carry out than the prior art, multi-step Seldinger technique, especially when using real-time ultrasound guidance. Accordingly, the apparatus of the invention is easier and safer to use for the patient, and much more comfortable for both the operator and the patient. Finally, the provision of at least one or multiple channels in the adapter renders the apparatus very compact.

The delivery apparatus may be arranged in use for delivering a catheter or cannula into a blood vessel, for example an artery or vein. Catheters and cannulae are devices that can be inserted into a body cavity, duct or vessel, to allow drainage, administration of fluids or gases, or access by surgical instruments. Generally, when the device is longer than about 10 cm, it is referred to as a catheter, and when it is shorter than about 10 cm, it is known as a cannula.

Thus, the apparatus may, for example, be used for introducing the catheter or cannula into a large vein in the neck, chest or groin of the subject, or for access to other vessels or body cavities. Preferably, the delivery apparatus is operable in use for the insertion of a central venous catheter (CVC). A CVC may also be referred to as a central line, a central venous line or a central venous access catheter.

The apparatus may also be used to obtain a blood sample, administer medication or fluids and/or directly obtain cardiovascular measurements, such as central venous pressure. The apparatus may also be used as single lumen device for measuring the pressure inside a vessel or to drain a body cavity.

The apparatus may be arranged in use to be introduced into the subject either with or without real-time ultrasound guidance.

Preferably, the distal end of the stellate is substantially blunt-ended (i.e. it is not bevelled or sharp). Advantageously, this makes the needle tip less traumatic while advancing the needle further inside the vessel after it has pierced the vessel's outer wall and entered its lumen. In addition, the stellate prevents biological material from the subject entering the channel of the needle, as it is inserted into the subject. Preferably, the stellate is substantially hollow. Thus, the stellate may comprise a channel extending therethrough. The channel may be arranged in use to aspirate fluid from the subject, such as blood. Alternatively, the channel may be arranged in use to be connected to a pressure transducer in order to measure pressure inside the vessel near the needle tip during the insertion procedure.

The stellate preferably comprises at least one aperture disposed at least adjacent its distal end, wherein the aperture is connected to the channel. The aperture may be disposed either on the end of the stellate (i.e. at the tip), or on the side of the stellate. In one embodiment, the stellate comprises a first aperture on its end, and a second aperture on its side. Advantageously, having two apertures, and especially the one on the side of the stellate (12), decreases the chances of it becoming blocked while being pushed into the patient. In addition, two apertures will reflect more ultrasound waves, and will enhance conspicuity of the apparatus under ultrasound.

Preferably, the stellate is moveable between a first (i.e. retracted) position in which its distal end does not extend beyond the distal end of the needle, and a second (i.e. extended) position in which its distal end extends beyond the distal end of the needle. The stellate may be moveable back and forth between the first and second positions, and this movement may be achieved either manually or via actuation means. Thus, the stellate is preferably retractable.

Preferably, the apparatus comprises biasing means for biasing the stellate into either the first position or the second position. Preferably, the biasing means biases the stellate into the first position, i.e. the retracted position. The biasing means preferably comprises a spring, for example a compression or helical spring. The apparatus preferably comprises an actuation means which is arranged, in use, to be actuated by an operator to urge the stellate between the first and second positions. The actuation means may comprise a trigger.

Thus, by depressing the actuation means (i.e. the trigger), the stellate may be pushed through the needle against the biasing force of the biasing means (i.e. the spring) so as to convert the sharp, bevelled end of the needle into a blunt tip, as shown in the configuration represented in FIG. 6A. Immediately prior to use, the stellate may be retracted in to the needle by re-pressing the actuation means, as shown in FIG. 6B.

Advantageously, the provision of a retractable stellate allows the clinician to choose when the sharp, bevelled end of the needle is presented to the subject, or when it is blunt-ended. This helps with the insertion technique, as initially the needle tip is required to be sharp or bevelled to enable piercing of the subject's skin and vessel wall until it reaches the vessel's lumen. This initial step may be carried out under ultrasound guidance. However, once the needle tip is inside a vessel lumen, the needle tip may then be converted into a blunt-ended tip before inserting it any further. This reduces the chances of migration/misplacement of the needle tip outside the lumen of the blood vessel during the insertion procedure, e.g. by accidently puncturing the vessel wall.

Preferably, the needle extends through the centre of the catheter or cannula, thereby forming a primary channel for direct access to a vessel or body cavity of the subject via the stellate, when the needle is subsequently removed. The primary channel may be attached, in use, to a syringe or pressure transducer via a tube or both. Preferably, however, the catheter or cannula comprises one or more additional (ancillary) channels extending therethrough, each of which allows direct access to the subject's vessel or body cavity. For example, the catheter or cannula may comprise at least one, two, three, four or five channels extending therethrough. The or each channel may comprise a one way valve to temporarily block or prevent spillage of fluid (e.g. blood), or the aspiration of air.

In one embodiment, the one or more additional channel may have a smaller diameter than the primary channel, but it will be appreciated that this does not always have to be the case. The one or more ancillary channel may be arranged radially around the circumference or peripheral edge of the catheter or cannula. For example, the catheter or cannula may comprise the primary channel with a pair of mutually opposing ancillary channels arranged radially therearound, preferably at different distances from the centre of the catheter or cannula. Alternatively, the catheter or cannula may comprise the primary channel with two pairs of mutually opposing ancillary channels arranged radially therearound. The number of ancillary channels depends on the type of work that the clinician intends to carry out on the subject, and how many separate entry sites into the vessel or body cavity are required.

Preferably, the adapter comprises a corresponding number of channels as is provided in the catheter or cannula, which, when aligned, each form a continuous passageway for providing direct access to the vessel or body cavity. For example, the adapter may comprise a main channel extending therethrough which is arranged in use to be aligned with the primary channel of the catheter or cannula. The adapter may comprise one or more additional (ancillary) channels extending therethrough, each of which is arranged to be aligned with an ancillary channel of the catheter or cannula. Thus, the adapter may comprise at least one, two, three, four or five channels extending therethrough for alignment with and attachment to a corresponding channel in the catheter or cannula. Once these channels have been aligned with the channels in the catheter or cannula, this results in the opening of the valves, if present, provided in the primary and ancillary channels of the cannula or catheter. Each channel of the adapter may comprise a feed tube and/or an associated end port via which pressures inside the vessel or body cavity can be monitored, or blood samples may be taken, or through which drugs may be introduced etc.

The method may comprise initially locating the vessel (i.e. a blood vessel) or body cavity using ultrasound. The end of the needle may then be advanced through a skin entry site of the subject until fluid (e.g. blood) is aspirated, and its position may be confirmed using either real-time ultrasound imaging, monitoring pressure and/or by measuring the fluid inside the vessel. The bevelled end of the needle may be presented to the subject by depressing the actuation means (i.e. trigger) such that the blunt end of the stellate is disposed in the retracted position while inserting the needle through the skin to the inside of vessel lumen. The method may comprise ensuring that the bevelled end of the needle is correctly positioned within the interior of the vessel using ultrasound and/or by monitoring the colour of the blood, pressure inside the lumen and/or the rate of its flow in order to distinguish between arterial and venous blood.

The needle may then be held in position while the blunt end of the stellate is advanced beyond the bevelled end of the needle by pressing the actuation means. The needle with a blunt bevel may then be advanced further inside the lumen of the vessel so as to place at least part of catheter or cannula inside the lumen or body cavity. The needle may be held in position and, using either an actuation device or simply by sliding it in, the needle tip, including the blunt stellate, may be retracted such that it lies inside the catheter or cannula. Alternatively, the catheter or cannula may be advanced along the shaft of the needle until it has entered some distance inside the vessel or cavity beyond the blunt needle tip. Advantageously, a tapered end of the catheter or cannula ensures the gradual access of the catheter/cannula into the blood vessel. The method may comprise moving the catheter or cannula further along inside the vessel or body cavity until it has reached its desired position. The needle and stellate may then be removed from the subject. Throughout the procedure, real-time ultrasound may be used for guidance and/or the central lumen of device (i.e. the hollow blunt stellate) may be connected to a syringe for fluid aspiration or to a pressure transducer for the measurement of pressure or to display a wave form to assist in the proper placement of the apparatus inside the vessel or body cavity.

Subsequently, the adapter may then be aligned with, and secured to, the proximal end of the catheter or cannula by aligning the at least one channel in the adapter with the corresponding channel in the catheter or cannula. Afterwards, a section of the catheter or cannula at least adjacent to the vessel entry site or adapter may then be fastened to the subject, for example by a suture or tape. The clinician may then take a blood sample, infuse or drain fluid (e.g. drugs), monitor central venous pressure and/or conduct cardiac applications etc.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

Referring to FIGS. 2-6, there are shown various representations of a central venous catheter (CVC) apparatus (1), which can be used by a clinician to gain access to the venous vasculature of a patient (not shown) for fluid infusion, blood sampling, central venous pressure monitoring and/or cardiac applications. The apparatus (1) essentially consists of two main components: (i) a cannula (23), which is inserted into a vein of the patient, and (ii) a mutually engageable outer catheter adapter (31), which is shown in FIG. 5A, and which is used to infuse fluids (e.g. drugs) to the patient, for taking a blood sample, or for attaching pressure monitoring apparatus etc. In use, the clinician first inserts the cannula (23) into the patient, and then once it is in position, the catheter adapter (31) is attached thereto by which direct access to the patient is achieved.

Referring to FIGS. 2A and 2B, there is shown the cannula (23) consisting of a narrow, elongate catheter section (16) attached to a cylindrical hub section (24). The diameter of the hub (24) is greater than that of the catheter (16). A conventional needle (14) extends through the centre of the hub (24) and the catheter (16), thereby forming a primary channel (17) therebetween, for direct access to a blood vessel of the patient, when the needle (14) is later removed. The needle (14) has a sharp bevelled end (18) for piercing the patient's skin, although this can be modified to be blunt-ended by means of a slideably arranged inner hollow stellate (12), which extends through the central channel of the needle (14). The stellate (12) has a hollow blunt end (13) and is provided to make the needle (14) less traumatic once it is inside the lumen of a blood vessel, and also to prevent biological material from the patient entering the channel of the needle (14) as the needle (14) is inserted into the patient. Also, this blunt tipped (13) stellate (12) is hollow, and has a continuous lumen extending therethrough, which can be connected to a syringe for aspiration of blood or fluid, or to a pressure transducer for measurement of pressure, or to produce a wave form display on a monitor (not shown).

Figure 6:
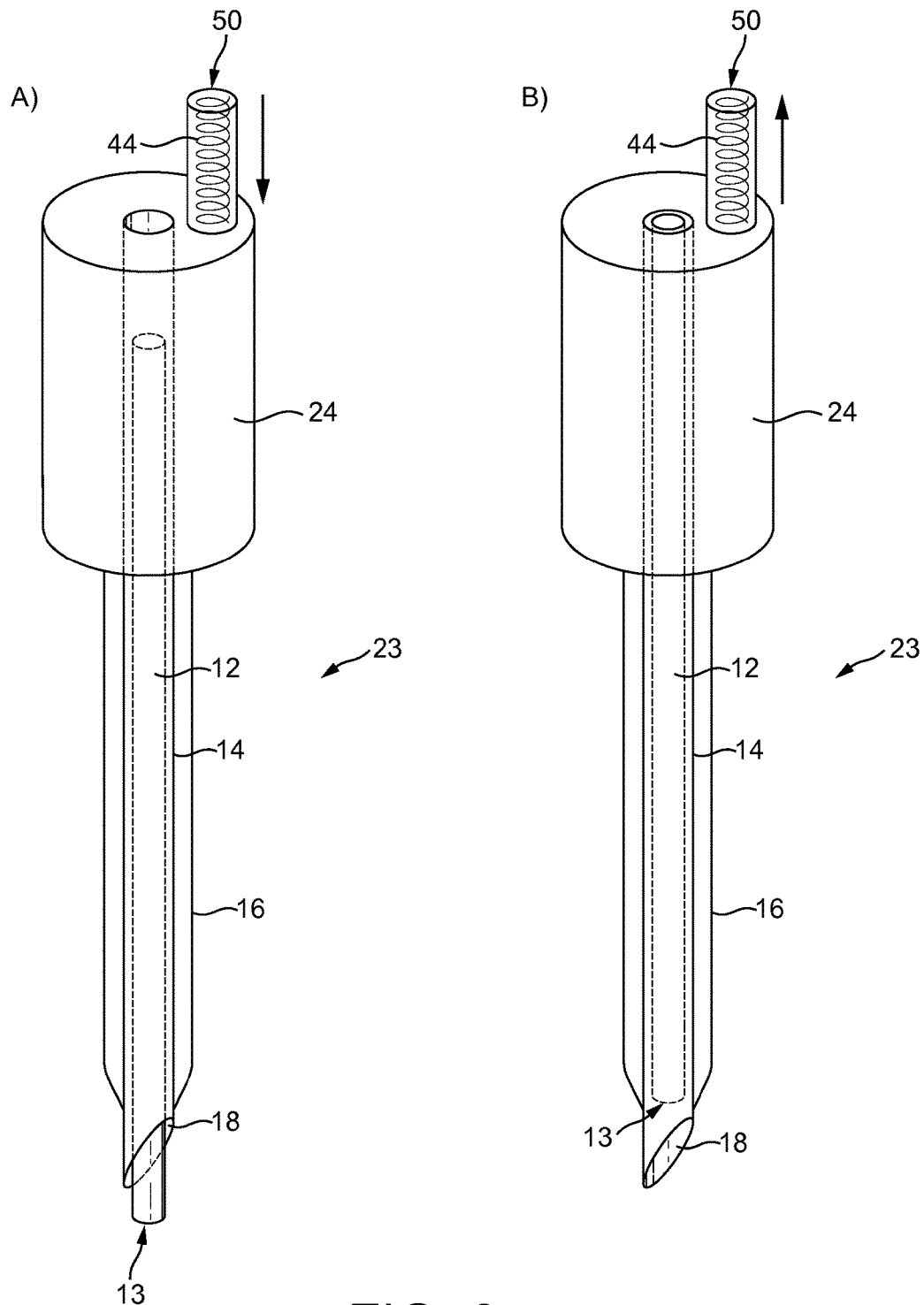
FIG. 6A is a perspective side view of the cannula showing a stellate extending out of a needle.
FIG. 6B shows the stellate in a retracted position.

FIG. 2B is a cross-section of the apparatus (1), and illustrates the mutual arrangement of the stellate (12), the needle (14) and the catheter (16) along axis C-C shown in FIG. 2A. As shown in FIG. 6, the respective positions of the stellate (12) in the needle (14) can be moved back and forth either manually, or by the action of a spring (44) and its associated trigger (50), as described later.

Figure 3:
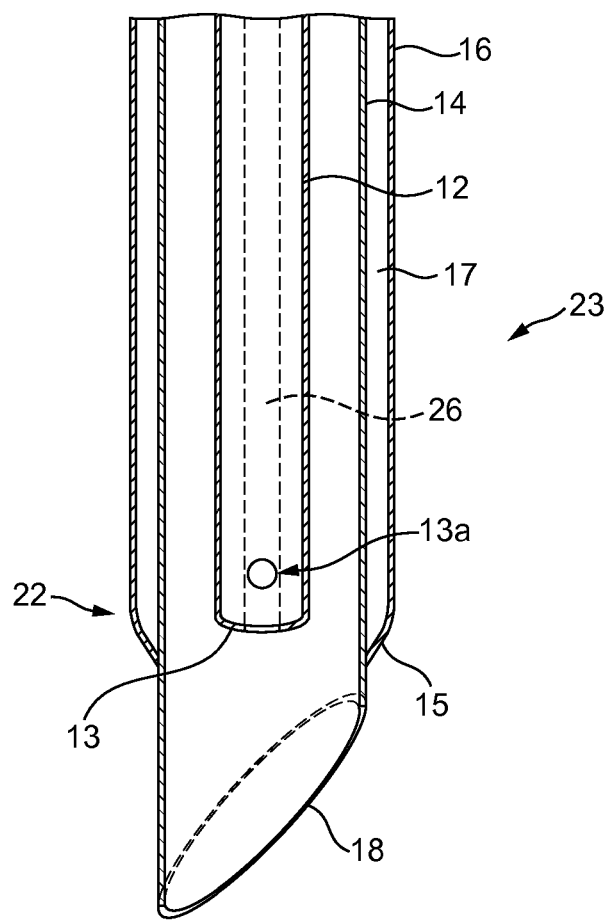
FIG. 3 is an enlarged cross-sectional side view of a distal end of the cannula shown in FIG. 2.
Figure 4:
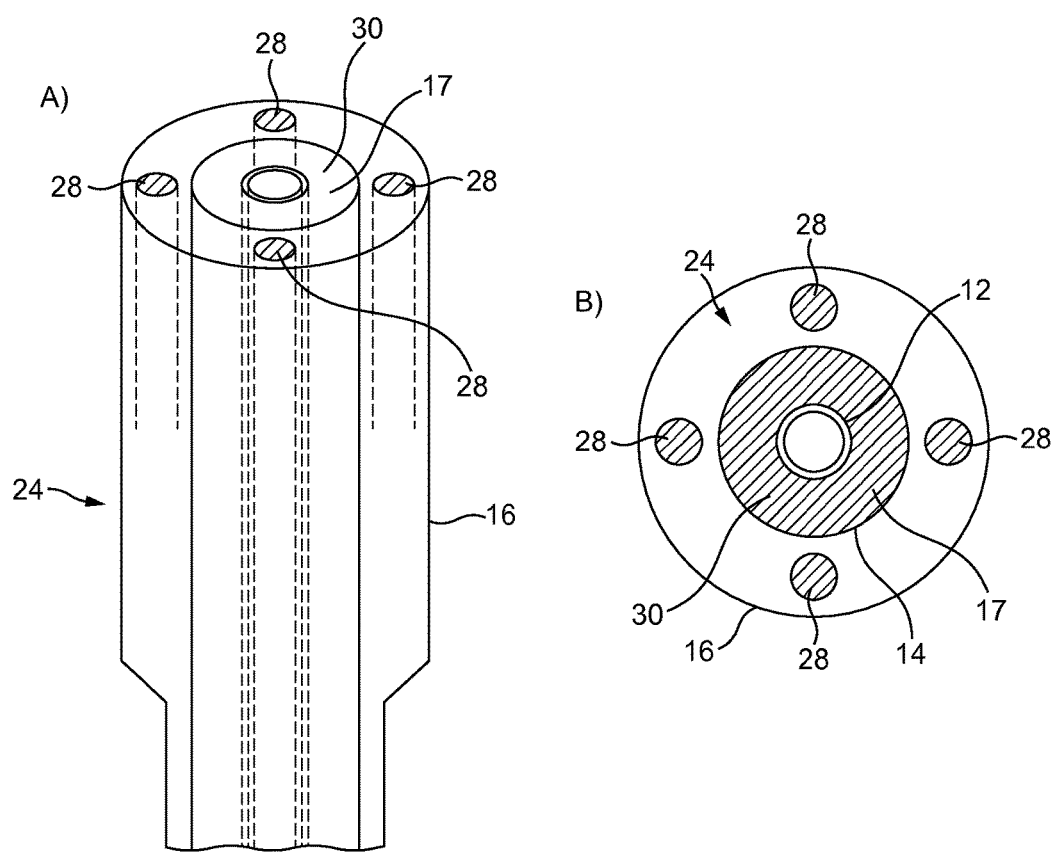
FIG. 4A is an enlarged cross-sectional perspective view of a proximal end of the cannula shown in FIG. 2.
FIG. 4B is cross-sectional plan view of the proximal end of the cannula shown in FIG. 4A.
Figure 5:
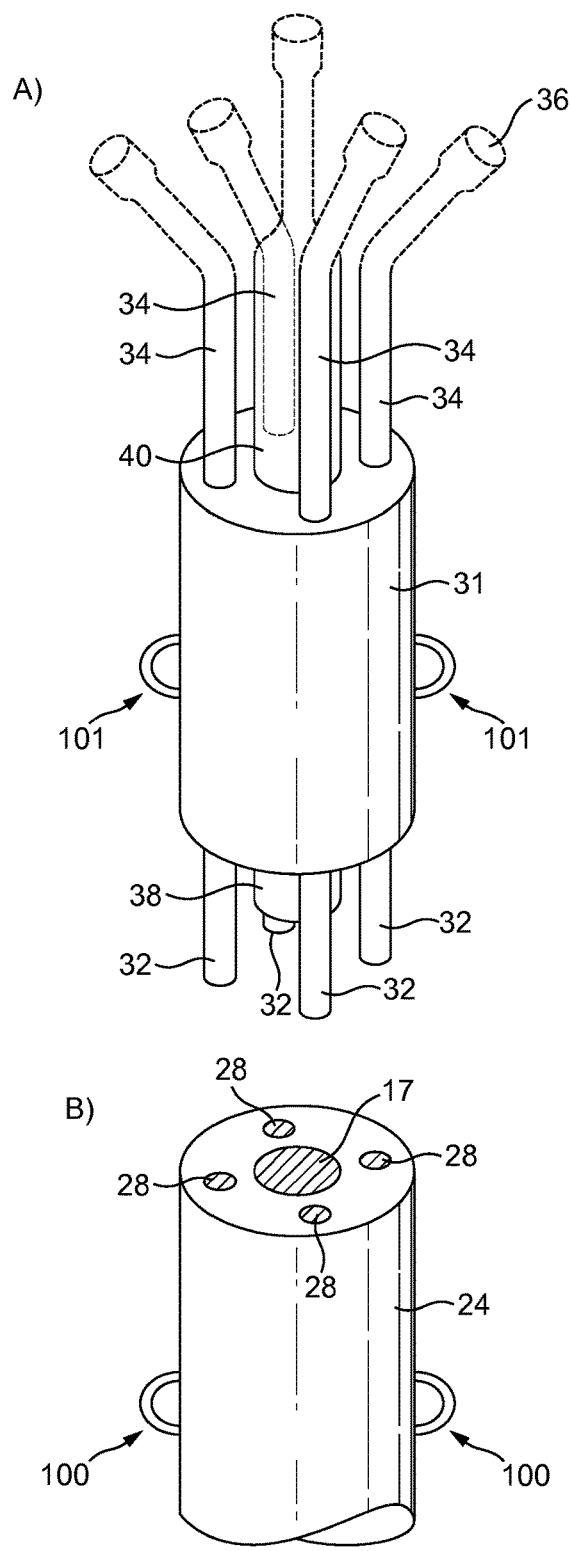
FIG. 5A is an enlarged perspective view of an outer catheter assembly of the apparatus of the invention.
FIG. 5B is an enlarged perspective view of the proximal end of the cannula shown in FIG. 4B.

FIG. 3 is an enlarged view of the distal end of the cannula (23) showing the respective arrangement of the slidable inner stellate (12), the needle (14) and catheter (16). The stellate (12) is hollow having an inner channel (26), and has a communicating distal blunt end (13). The stellate (12) has two apertures, the first one being at the distal tip of thereof, and the second aperature (13a) being disposed on one side of the tip of the stellate (12). Having two apertures, and especially aperture (13a) on the side of the stellate (12), decreases the chances of becoming blocked while being pushed into the patient. Also, the apertures will reflect more ultrasound waves, and will enhance conspicuity of the apparatus (1) under ultrasound, as will be described below. FIG. 3 shows the stellate in a retracted position in which it does not extend beyond the bevelled end (18) of the needle (14). The distal tip (22) of the catheter (16) does not extend beyond the end (18) of the needle (14).

Referring to FIGS. 4A and 4B, there is shown the hub section (24) of the cannula (23) in detail. In addition to the primary channel (17) extending through the catheter (16) when the needle (14) and stellate (12) have been removed, the catheter (16) also includes one or more additional ancillary channels (28) extending therethrough. In the embodiment shown, the additional channels (28) have a smaller diameter than the primary channel (17), but it will be appreciated that this does not always have to be the case, and their diameter may be the same as, or even larger than the primary channel (17). As shown most clearly in FIG. 4B, the hub (24) includes the central channel (17) with two pairs of mutually opposing ancillary channel (28) arranged radially therearound. The number and diameter of ancillary channel (28) depends on the type of work the clinician intends to carry out on the patient, and how many ports or entry sites into the vein or vessel are required. These channels (28) on the catheter (16) each have a one-way valve (not shown) to stop blood coming out, or air getting sucked in, when the lumens are left open.

FIG. 5A schematically illustrates the outer catheter adapter (31), which is substantially tubular in shape, and arranged to be attached to the hub section (24) of the cannula (23). In cross section, the hub (24) and adapter (31) can be either round or oval or slightly flattened. Having an oval-shaped cross section can help in visualisation of the hub (24) and adapter (31) under ultrasound because it will reflect more ultrasound waves. Hub (24) includes two laterally extending side wings or flanges (100), and adapter (31) also has two laterally extending wings or flanges (101). These flanges (100, 101) are used to fasten the device (1) to the patient by, for example, a suture and/or adhesive tapes. Extending out of the centre of a distal end of the catheter adapter (31) there is provided a central tube (38), which is arranged to be inserted into the central channel (17) of the hub (24), as shown in FIG. 5B. Similarly, extending radially out of the distal end of the adapter (31) there are four smaller outer tubes (32), which are arranged to be inserted into the outer ancillary channels (28) of the hub (24). Extending out of the proximal end of the catheter adapter (31) there is provided an inner feed tube (40), and a series of outer feed tubes (34), and associated end ports (36) via which pressure may be monitored or blood samples may be taken, or through which drugs may be introduced etc.

Referring to FIG. 6, there is shown an embodiment of the apparatus (1) which includes a spring assembly (44) provided inside the hub (24), and an associated trigger (50), which together are used to alter the position of the stellate (12) inside the needle (14) between an extended position (see FIG. 6A) and a retracted position (see FIG. 6B). By depressing the trigger (50), the stellate (12) is pushed through the needle (14) against the biasing force of the spring assembly (44) so as to convert the sharp, bevelled end of the needle (18) into a blunt tip, as shown in the configuration represented in FIG. 6A. Immediately prior to use, the stellate (12) can be retracted in to the needle (14) by re-pressing the trigger (5), as shown in FIG. 6B, to form a sharp bevel. However, once the needle tip (18) is inside the lumen of the vessel, by depressing the trigger (50), the stellate (12) is pushed through the needle (14) against the biasing force of the spring assembly (44) so as to covert the sharp bevelled end of the needle (18) into a blunt tip to reduce the chances of accidental migration of the needle tip (18) outside the lumen (as a sharp bevel has a greater chance of puncturing the vessel wall compared to a blunt tip needle) and subsequently the needle (14) is advanced further inside the vessel.

Figure 7:
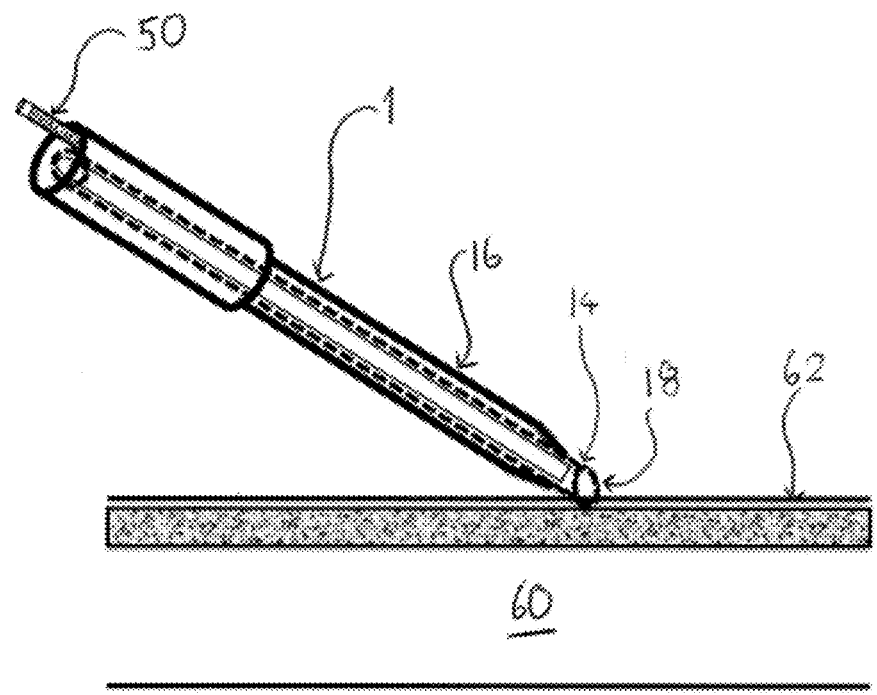
FIG. 7 illustrates how the apparatus of the invention may be used to gain access to the venous vasculature of a patient by steps A-G.
Figure 7:
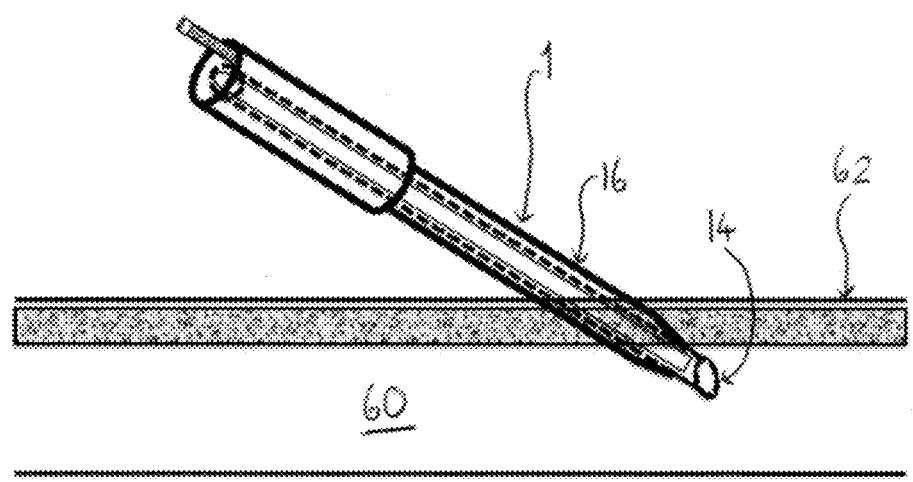
Figure 7:
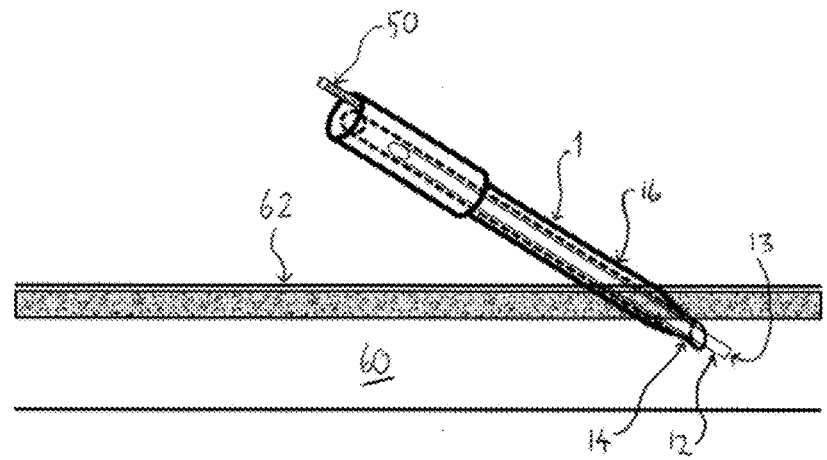
Figure 7:
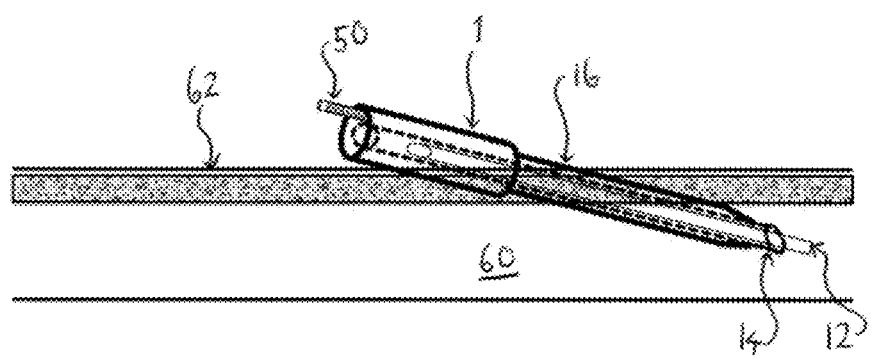
Figure 7:
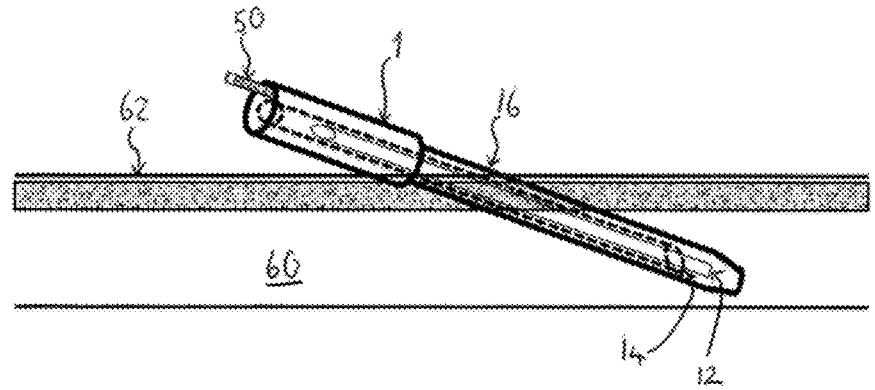
Figure 7:
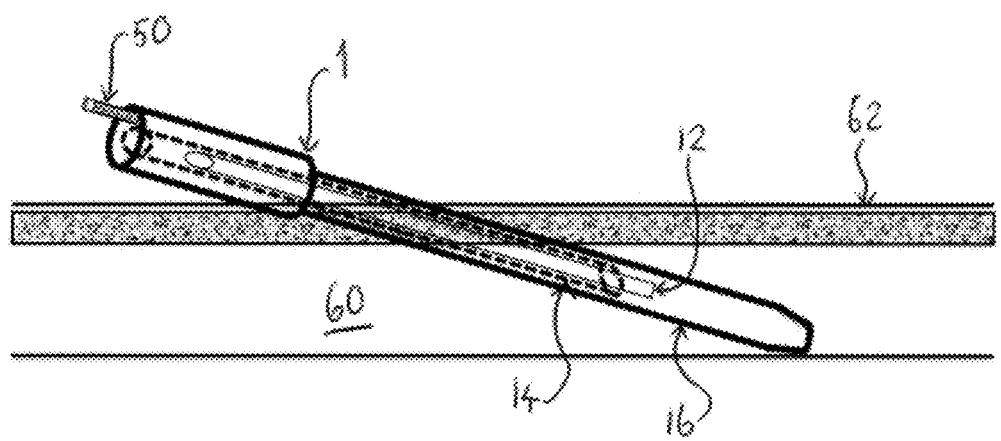
Figure 7:
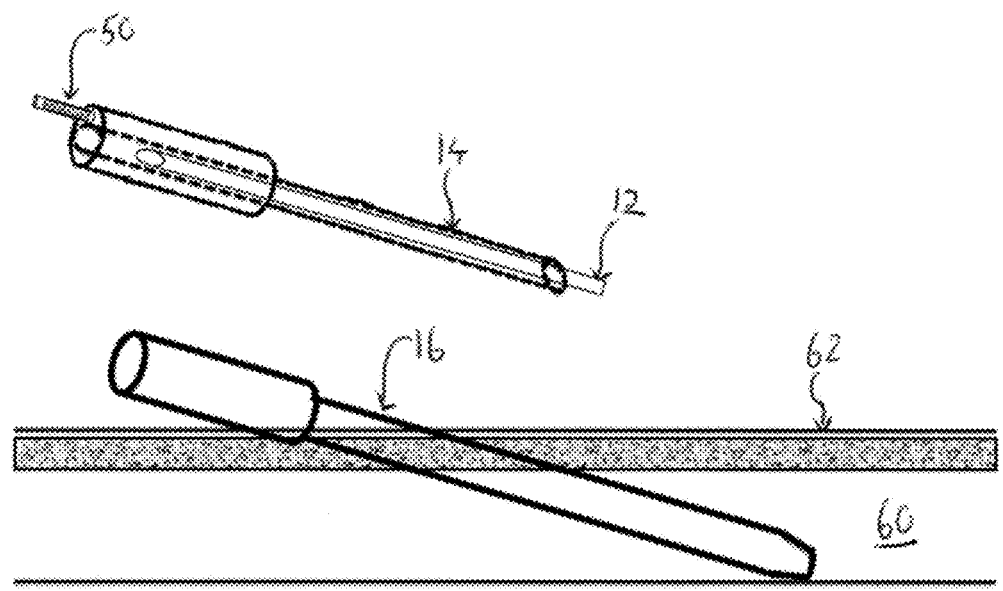

Use of the apparatus (1), as shown in FIGS. 7A and 7B, will now be described in detail. Firstly, after the location of a vein (60) has been identified by using ultrasound or various markers, the bevelled end (18) of the needle (14) is advanced through the skin (62) entry site until the needle tip is inserted inside the vessel (60). Ultrasound imaging and/or blood is aspirated to confirm the placement of the needle tip. As discussed above in relation to FIG. 6, the sharp bevelled end (18) of the needle (14) is presented by depressing the trigger (50) such that the blunt end (13) of the stellate (12) is in the retracted position shown in FIGS. 6B, 7A and 7B. To ensure that the bevelled end (18) of the needle (14) is positioned within the interior of the vein (60) (and has not advanced too far), the confirmation of placement is achieved using real-time ultrasound imaging as well as looking for additional supporting evidence, such as the colour of aspirated blood, the pressure inside the lumen, the rate of its flow etc. to differentiate between arterial and venous cannulation. Real time ultrasound imaging is normally used to perform this procedure.

The needle (14) may then be held in position and the blunt end (13) of the stellate (12) is advanced beyond the bevelled end (18) of the needle (14) by pressing the trigger (50), as shown in FIG. 7C. Now, as shown in FIG. 7D, the needle (14) with a blunt end is advanced further inside the lumen of vessel (60) so as to place a part of catheter (16) inside the lumen. The needle (14) may be held in position again, while the catheter (16) is further advanced along the shaft of the needle for a required distance until it has entered some distance beyond the blunt needle tip inside the lumen, as shown in FIG. 7E. The tapered end (15) of the catheter (16) ensures the gradual access of the catheter (16) into the blood vessel. The method may comprise moving the catheter (16) along with partially withdrawn needle (14) and stellate (12), and further along inside the vein until it has reached its desired position, as shown in FIG. 7F. The needle (14) and stellate (12) may then be removed from the subject, as shown in FIG. 7G. Throughout the procedure the central lumen (26, 17) of the device (i.e. the hollow blunt stellate 13) can be connected to a syringe for aspiration of blood, or to a pressure transducer for display of pressure wave form or measurement of pressure inside the vessel in order to assist the proper placement of the device along with the use of real time ultrasound imaging.

Afterwards, wings (100), which extend out of the catheter hub (24) immediately adjacent to the vessel entry site, can be fastened to the patient by, for example, a suture and/or adhesive tapes. Finally, if not already attached, the catheter adapter (31) is then aligned with and secured to the hub (24) of the cannula (23) by aligning tube (38) with primary channel (17) and tubes (32) with ancillary channel (28). The wings (101) on the catheter adapter (31) can also be fastened to the patient by, for example, a suture and/or adhesive tapes. The clinician can then take blood samples, infuse or drain fluids (e.g. drugs), monitor central venous pressure and/or conduct cardiac applications with the fitted CVC apparatus (1).

SUMMARY

Central venous catheters are used for drug delivery and the measurement of pressure in central veins. Also, arterial cannulae are inserted inside the lumen of arteries, especially radial, femoral or brachial artery in order to measure invasive arterial pressure and for extracting blood samples for investigation. Currently available catheters and cannulae are designed to be used with landmark guided "blind" techniques. However, with the introduction of ultrasound, there is a need to have purpose built catheters/cannulae. Prior art central venous catheters require a venous access apparatus (i.e. needle, cannulae, guidewire and dialator) and the catheter itself with extension tubes. However, the apparatus of the invention (1) provides a delivery apparatus which incorporates part of the catheter (23) itself, and after removing the needle (14) and the stellate (12), a catheter adapter (31) which is simply connected to the catheter (23) and secured in position on the patient. Hence, the invention includes the catheter (23), the delivery apparatus and also the catheter adaptor (31).

Advantages of the CVC (1) reside in the fact that the cannula (23) component of apparatus (1) can be simply introduced into the vein or artery of a patient in effectively a single-step procedure especially while using real-time ultrasound guidance, which is significantly easier to carry out than the prior art Seldinger technique, which is illustrated in FIG. 1. Also, the outer catheter adapter (31) can be easily mounted to convert the whole assembly into a single or multiple lumen device. Using real time ultrasound guidance with the Seldinger technique can be quite cumbersome and difficult, as then there is need for two operators, one for holding the ultrasound probe and the second for performing the needling technique. Alternatively, one needs to remove the ultrasound probe a few times during the procedure. Also, the new CVC apparatus (1) of the invention does not require the use of a guidewire, minimizing the need for drapes, and the procedure can be performed relatively quickly using an asepsis technique, an added advantage in emergency situations. Thus, the apparatus (1) is much quicker and safer to use, simple and more comfortable for the operator and for the patient.

The provision of the retractable stellate (12) allows the clinician to choose when the sharp bevelled end (18) of the needle (14) is presented to the patient, or when it is made blunt-ended. This increases the safety of the apparatus (1) when not in use and also while doing the procedure (as described above), but can be quickly and easily transformed into a sharp end (18) when needed. Furthermore, the hollow stellate provides a channel (26), which can be easily connected via a tube to a pressure transducer and/or a syringe or both. The blunt end has a central hole and the hub end has a port for connection to a pressure transducer or syringe. Thus, it is possible to aspirate blood (via syringe) or obtain a pressure wave form display and pressure readings (e.g. 110/80 for arterial blood or 12/4 for a central vein) on a monitor. This assists the clinician in addition to ultrasound imaging by (a) differentiating the nature of the vessel, i.e. whether the needle tip is inside a high pressure artery or a low pressure vein, and (b) by looking at the waveform while inserting the needle further inside the lumen of the vessel (e.g. radial artery), it is possible to confirm that it is being advanced in the right direction.

Currently, no arterial cannulae or venous catheters exist which have:—(i) a blunt tip (in order to reduce trauma and facilitate insertion of the needle further inside the lumen of vessel), and (ii) hollow lumen (in order to measure the pressure at the tip of needle while puncturing the vessel in order to check if it has penetrated a vein or artery, i.e. low or high pressure conduit). The blunt tip of the stellate is on the needle tip side and the other end of stellate is on the needle hub side, where the hollow stellate can be connected to a pressure transducer for pressure measurement. The pressure inside the vessel has two purposes:—(a) it confirms the placement of needle tip inside the vessel to assist the insertion of the needle further, e.g. when pressure waveform is lost during insertion, the clinician will know that the needle is deviating from its path and so needs a slight re-adjustment; and (b) it confirms that the needle tip is placed in the correct vessel, i.e. artery or vein. This is a standard protocol followed by clinicians while inserting central venous catheters before further dilatation of the vessel.

Although the above examples predominantly describe the use of central venous access, the invention can also be used for arterial cannulae because the same needle with single lumen cannulae having a smaller size would be suitable for use with ultrasound guided arterial cannulation. It will be appreciated that when the plastic tube being inserted into the vessel is longer than 10 cm, then it is referred to as a catheter. When the tube is less than 10 cm, it is known as a cannula.

The invention claimed is:
1. A delivery apparatus for introducing a catheter or cannula into a subject's vessel or body cavity, the apparatus comprising:
   (i) a hub comprising a proximal end and a distal end,
   (ii) a catheter or cannula attached to the distal end of the hub and comprising at least one channel extending therethrough and through which access to a subject's vessel or body cavity is achieved,
   (iii) a removable needle, comprising a distal end, extending through the catheter or cannula and the hub, the needle comprising a stellate concentric on the same axis of the needle, slideably disposed therein, and moveable between a first, retracted position in which its distal end does not extend beyond the distal end of the needle, and a second, extended position in which its distal end extends beyond the distal end of the needle;
   (iv) biasing means, provided inside the hub, for biasing the stellate into the first, retracted position; and
   (v) an actuator comprising a trigger which is disposed on the hub and arranged, in use, to be actuated by an operator to urge the stellate between the first and second positions, wherein the stellate is configured to move from the first, retracted position to the second, extended position when the trigger is depressed by the operator, and wherein the stellate does not move between the first, retracted position and the second, extended position automatically or when the trigger is released.

2. An apparatus according to claim 1, wherein the catheter is a central venous catheter (CVC).

3. An apparatus according to claim 1, wherein the apparatus is arranged, in use, to be introduced into the subject with real-time ultrasound guidance.

4. An apparatus according to claim 1, wherein the distal end of the stellate is substantially blunt-ended.

5. An apparatus according to claim 1, wherein the stellate comprises a channel extending therethrough.

6. An apparatus according to claim 5, wherein the channel is arranged in use to aspirate fluid from the subject.

7. An apparatus according to claim 5, wherein the channel is arranged in use to be connected to a pressure transducer in order to measure pressure inside the vessel near the needle tip during the insertion procedure.

8. An apparatus according to claim 1, wherein the biasing means comprises a spring.

9. An apparatus according to claim 1, wherein the needle extends through the center of the catheter or cannula, thereby forming a primary channel for direct access to a vessel or body cavity of the subject when the needle and stellate are subsequently removed.

10. An apparatus according to claim 9, wherein the primary channel is attached, in use, to a syringe or pressure transducer via a tube or both.

11. An apparatus according to claim 9, wherein the catheter or cannula comprises one or more additional channels extending therethrough, each of which allows direct access to the subject's vessel or body cavity.

12. An apparatus according to claim 11, wherein the catheter or cannula comprises at least two channels extending therethrough.

13. An apparatus according to claim 11, wherein each of the channels comprises a one way valve to temporarily block or prevent spillage of fluid, or the aspiration of air.

14. An apparatus according to claim 1, further comprising:
(vi) an adapter comprising at least one channel extending therethrough, and arranged, in use, to be attached to the catheter or cannula following removal of the needle and stellate from the subject, such that the at least one channel in the adapter aligns with the at least one channel in the catheter or cannula to thereby create at least one continuous passageway through which access to the subject's vessel or body cavity is achieved.

15. A method for obtaining a sample from a subject, or draining fluid from a subject, or administering medication or fluid to a subject, or monitoring a subject, or for carrying out a cardiovascular measurement on a subject, the method comprising use of the delivery apparatus according to claim 1.

16. A method for introducing a catheter or cannula into a vessel or body cavity of a subject, the method comprising: attaching the delivery apparatus according to claim 1 to a subject, and introducing the catheter or cannula into the vessel or body cavity.

17. The method of claim 16, further comprising:
(i) causing the stellate of the apparatus of claim 1 to move to the first, retracted position;
(ii) advancing the distal end of the needle through skin;
(iii) confirming the placement of the needle tip using real-time ultrasound imaging;
(iv) causing the stellate to move to the second, extended position; and
(v) advancing the distal end of the needle further in the vessel or body cavity to thereby introduce the catheter or cannula in the vessel or body cavity.

18. The method of claim 17, further comprising after step (v):
(vi) advancing the catheter or cannula along the needle until the catheter or cannula has passed a distance beyond the distal end of the needle;
(vii) removing the needle and stellate; and
(viii) fastening the catheter or cannula to the patient.

19. An apparatus according to claim 14, wherein the adapter comprises a corresponding number of channels as is provided in the catheter or cannula, which, when aligned, each form a continuous passageway for providing direct access to the vessel or body cavity.

* * * * *